United States Patent
Chang et al.

(10) Patent No.: US 11,938,272 B2
(45) Date of Patent: Mar. 26, 2024

(54) RESPIRATORY MASK

(71) Applicant: MacKay Memorial Hospital, Taipei (TW)

(72) Inventors: Wen-Han Chang, Taipei (TW); Shih-Yi Lee, Taipei (TW); Ren-Jei Chung, Taipei (TW); Ching-Yu Kuo, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 994 days.

(21) Appl. No.: 16/776,281

(22) Filed: Jan. 29, 2020

(65) Prior Publication Data

US 2020/0268999 A1 Aug. 27, 2020

(51) Int. Cl.
*A61M 16/06* (2006.01)

(52) U.S. Cl.
CPC .... *A61M 16/0683* (2013.01); *A61M 16/0666* (2013.01); *A61M 2210/0625* (2013.01)

(58) Field of Classification Search
CPC .......... A61M 16/0683; A61M 16/0666; A61M 16/0672
See application file for complete search history.

(56) References Cited

U.S. PATENT DOCUMENTS

| | | | | |
|---|---|---|---|---|
| 69,396 A * | 10/1867 | Brayton | ................ | A61M 16/18 128/207.18 |
| 718,785 A * | 1/1903 | Mcnary | ............. | A61M 16/0666 128/207.18 |
| 853,439 A * | 5/1907 | Clark | ................ | A61M 16/0666 128/207.18 |
| 1,125,542 A * | 1/1915 | Humphries | ....... | A61M 16/0694 128/207.18 |
| 1,873,160 A * | 8/1932 | Sturtevant | ......... | A61M 16/0493 128/207.14 |
| 2,470,297 A * | 5/1949 | Fields | ................ | A61M 15/0013 128/203.15 |
| 3,291,121 A * | 12/1966 | Vizneau | ............ | A61M 16/0078 128/205.15 |
| 5,513,634 A * | 5/1996 | Jackson | ............ | A61M 16/0495 128/207.14 |

(Continued)

FOREIGN PATENT DOCUMENTS

EP 1695732 A1 * 8/2006 ........ A61M 16/0666

*Primary Examiner* — Michael J Tsai
(74) *Attorney, Agent, or Firm* — Sinorica International Patent & Trademark

(57) ABSTRACT

The present invention discloses a respiratory mask to connect a user and a breathing tube for receiving a first gas and releasing a second gas, so as to provide an user's respiratory system to exchange gas. It comprises a main part, an air chamber exchange part, an insert and a clamping part. The main part provides a first, second, and third openings that are communicated each other. The first opening connects to the breathing tube to receive the first gas from the breathing tube. The air chamber exchange part provides an exhaust assembly to relieve pressure according to an internal air pressure of the air chamber exchange part. The insert connects to the user's nose so as to direct the first gas to the user or direct the second gas from the user to the air chamber exchange part. The clamping part connects to the user's mouth.

11 Claims, 5 Drawing Sheets

(56) References Cited

U.S. PATENT DOCUMENTS

| | | | | |
|---|---|---|---|---|
| 5,645,046 A * | 7/1997 | Kay | ............... | A62B 9/06 128/207.14 |
| 5,752,510 A * | 5/1998 | Goldstein | ......... | A61M 16/0672 128/207.14 |
| 5,983,892 A * | 11/1999 | Thornton | ............... | A62B 9/06 128/206.29 |
| 6,405,729 B1 * | 6/2002 | Thornton | ......... | A61M 16/0493 433/7 |
| 6,505,623 B1 * | 1/2003 | Hansen | ............ | A61M 16/0683 128/207.11 |
| 7,676,276 B2 * | 3/2010 | Karell | ............. | A61M 16/0493 607/42 |
| 7,946,288 B2 * | 5/2011 | Flynn | .............. | A61M 16/12 128/207.14 |
| 8,534,278 B2 * | 9/2013 | Colman | ............ | A61M 39/22 128/207.14 |
| 9,610,189 B2 * | 4/2017 | Heinonen | ........ | A61M 16/0833 |
| 9,737,678 B2 * | 8/2017 | Formica | ............ | A61M 16/0825 |
| 11,065,410 B1 * | 7/2021 | Feld | ............. | A61M 16/0493 |
| 11,207,484 B2 * | 12/2021 | Heatherington | .. | A61M 16/0666 |
| 11,298,494 B2 * | 4/2022 | Barraclough | ....... | A61M 16/209 |
| 2005/0121037 A1 * | 6/2005 | Wood | ............. | A61M 16/0683 128/207.18 |
| 2006/0096600 A1 * | 5/2006 | Witt | ............... | A61M 16/0488 128/859 |
| 2006/0207597 A1 * | 9/2006 | Wright | ............ | A61M 16/0493 128/207.18 |
| 2006/0266359 A1 * | 11/2006 | Van Beurden | ...... | A61M 16/208 128/205.24 |
| 2008/0149105 A1 * | 6/2008 | Matula | ............ | A61M 16/0825 128/206.28 |
| 2008/0156330 A1 * | 7/2008 | Smith | ............. | A61M 16/0057 128/206.15 |
| 2008/0276938 A1 * | 11/2008 | Jeppesen | ........... | A61M 16/0605 128/204.18 |
| 2010/0218773 A1 * | 9/2010 | Thornton | ......... | A61M 16/0497 128/848 |
| 2010/0224197 A1 * | 9/2010 | Keropian | ......... | A61M 16/0488 128/848 |
| 2010/0311003 A1 * | 12/2010 | Kozlov | ............ | A61F 5/566 128/848 |
| 2010/0317987 A1 * | 12/2010 | Inoue | ............. | A61M 16/0683 600/543 |
| 2012/0325218 A1 * | 12/2012 | Brambilla | ......... | A61M 16/0833 128/205.25 |
| 2015/0040907 A1 * | 2/2015 | Hakim | ............ | A63B 23/18 128/205.24 |
| 2019/0240435 A1 * | 8/2019 | Anderson | ......... | A61M 16/0816 |

* cited by examiner

RESPIRATORY MASK

FIELD OF THE INVENTION

The present invention relates to the technical field of medical devices, particularly, it is a respiratory mask which assists a user's respiration cycle.

BACKGROUND OF THE INVENTION

Traditionally, when a patient is not prone to breath spontaneously, the patient is assisted by a breathing apparatus to perform a cycle of inhalation and ventilation. During the process, the patient's mouth and nose are covered by a mask. Exhalation and inhalation cannot be effectively exchanged in the same air chamber.

To expel the previous exhalation, there are several air holes in the traditional masks to remove exhaust gas (such as carbon dioxide); however, the pores are to avoid a large amount of gas leakage from the respirator, so in the design, the pore diameters of the pores are small, and the efficiency of the exhaust gas is remarkably poor.

In addition, the patient may inhale the exhaust gas and the fresh oxygen from the respirator into the lungs again before exhaling the exhaust gas which remains in the air chamber. The gas exchange efficiency becomes worse. Moreover, if the exhaust gas contains bacteria, it is concerned that the patient will get repeated infections.

In view of this, the present invention proposes a respiratory mask to solve the problems from the previous techniques.

SUMMARY OF THE INVENTION

The first object of this invention is to provide a respiratory mask, which contains a main part, an air chamber exchange part, an insert and a clamping part that can help receive the gas and release the exhaust gas to meet the purpose of reducing or avoiding exhaust gas mixed with the gas from the respirator.

The second object of this invention is to provide a respiratory mask, by separating at least two of the main part, the air chamber exchange part, the insert and the clamping part. According to the user's demand, the gas can be sent together or separately to the user's nose and mouth so as to provide the user with gas from, for example, a respirator.

The third object of this invention is based on a respiratory mask in which a user can pre-set an insert and a clamping part for quick attachment to or removal from the respirator.

The fourth object of this invention is that with positive pressure or negative pressure, the exhaust assembly provides a one-way air valve to quickly remove exhaust gas.

The fifth object of this invention is that exhaust assembly does not require additional power to achieve energy saving and environmental protection.

The sixth object of this invention is that this respiratory mask provides a user with different air chambers or airflow splitting to reduce or avoid the possibility of repeated infections.

The seventh object of this invention is that the clamping part can be stabilized inside a user's mouth unlike the respiratory mask mentioned above, which can disperse, slow down or eliminate the force of the main part and the air chamber exchange part on the user's nose.

The eighth object of this invention is that the insert has a sealed part which can closely stick to the user's nostrils to avoid gas leakage unlike the respiratory mask mentioned above.

To achieve the above and other objects, the invention provides a respiratory mask connected to a breathing tube for receiving a first gas and releasing a second gas to supply a user's motion of respiratory system. The respiratory mask comprises a main part, an air chamber exchange part, an insert, and a clamping part. The main part includes a first air chamber, a first opening, a second opening, and a third opening. The first opening and the second opening are communicated each other. The first opening connects to the breathing tube to receive the first gas from the breathing tube. The air chamber exchange part includes a second air chamber, an exhaust assembly, a fourth opening, and a fifth opening. An exhaust assembly is formed at the periphery of the air chamber exchange part. The fourth opening is jointed with the second opening. The exhaust assembly determines whether to communicate the second air chamber with the outside of the air chamber exchange part or not based on the internal and external air pressure of second air chamber. The insert connects to the fifth opening. The insert connects to the user's nose. The insert directs the first gas to the user or directs the second gas from the user to the second air chamber. The insert is a hollow body. The clamping part connects to the third opening. The clamping part connects to the user's mouth.

To achieve the above and other objects, the invention provides a respiratory mask that connects to a breathing tube for receiving a first gas and releasing a second gas to supply a user's motion of respiratory system. The respiratory mask includes a main part, an air chamber exchange part, an insert and a clamping part. The main part includes a first air chamber, a first opening, a second opening and a third opening. The first opening and the second opening is communicated each other through the first air chamber. The air chamber exchange part includes a second air chamber, an exhaust assembly, a fourth opening and a fifth opening. An exhaust assembly is formed at the periphery of the air exchange chamber part. The fourth opening connects the breathing tube to receive the first gas from the breathing tube. The fifth opening is jointed with the first opening. The exhaust assembly determines whether to communicate the second air chamber with the outside of the air chamber exchange part or not based on an internal air pressure and an external air pressure of the second air chamber. The insert connects to the first air chamber. The insert connects to the user's nose. The insert directs the second gas to the user or directs the second gas from the user to the first air chamber and the second air chamber. The clamping part connects to the third opening, and the clamping part connects to the user's mouth.

Compared to previous techniques, the invention provides a respiratory mask which has different modes of operation (e.g., first operation mode, second operation mode and third operation mode, etc.) to suit different situations. For example, in the first operation mode, the user can exhale and inhale only through nose; in the second operation mode, the user can exhale and inhale only through mouth; and, in the third operation mode, the user uses both mouth and nose to perform a respiration cycle.

DETAILED DESCRIPTION OF THE EMBODIMENTS

In order to fully understand the purpose, features, and effects of the present invention, the present invention will be described in detail with a description of the present embodiments and the accompanying drawings.

In present invention, "a" or "an" is used to describe the units, elements, and components described herein. This is done for convenience of description only and providing a general meaning to the scope of the present invention. Therefore, unless clearly stated otherwise, the description should be understood to include one, at least one, and the singular can also include plural.

In this invention, the terms "including", "having", "containing" or any other similar terms are intended to encompass non-exclusive inclusive. For example, a component, structure, article, or device that contains a plurality element is not limited to such elements as listed herein but may include those not specifically listed but which are typically inherent to the component, structure, article, or device. In addition, the term "or" means an inclusive "or" rather than an exclusive "or" unless clearly stated to the contrary.

Figure 1:
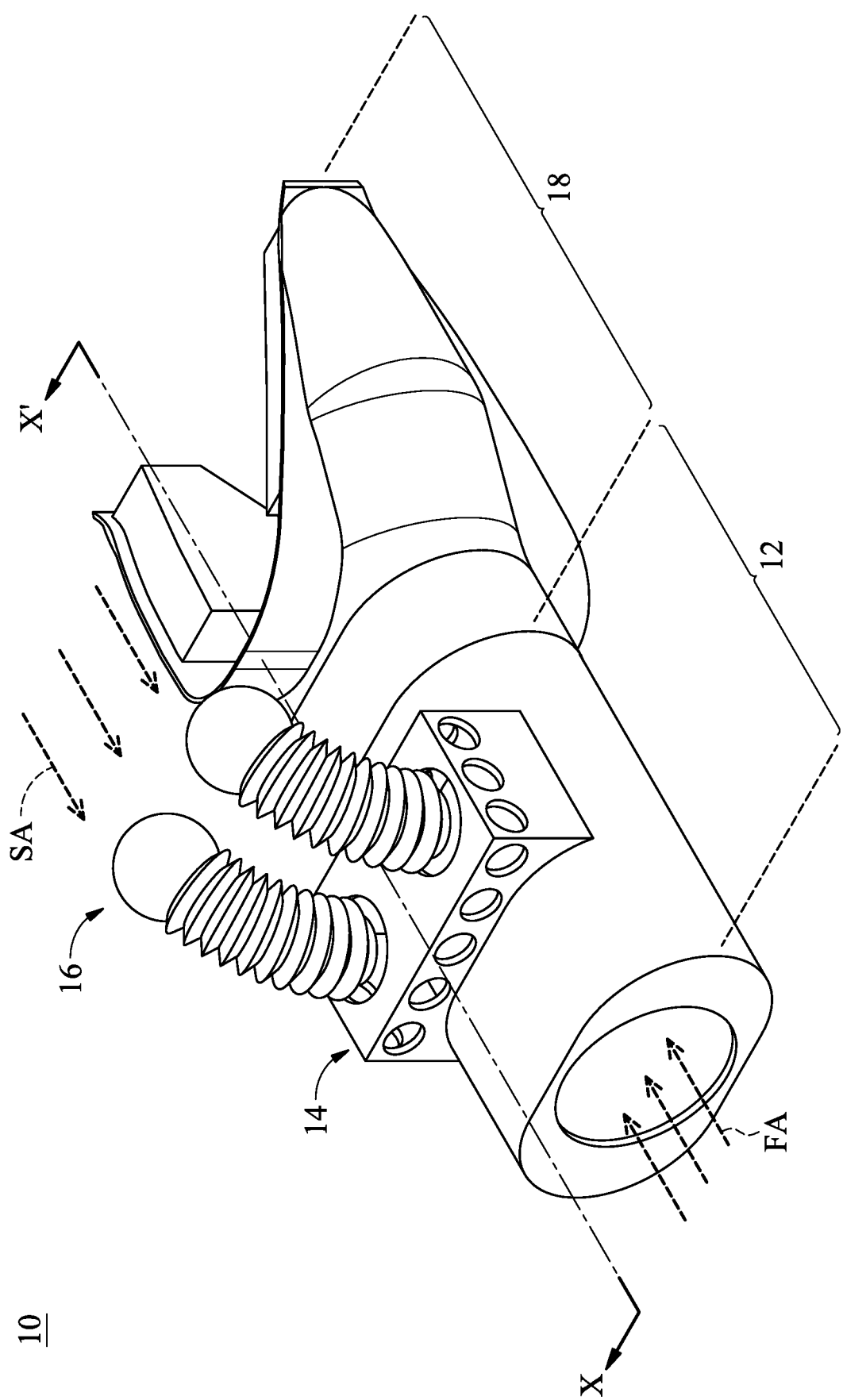
FIG. 1 is the stereograph of the respiratory mask of the first embodiment in the present invention.

Please refer to FIG. 1, a stereograph showing the structure of a respiratory mask according to a first embodiment of the present invention. In FIG. 1, the respiratory mask 10 connects to a breathing tube (not shown). In this embodiment, the breathing tube receives a first gas FA which is generated from a respirator. The respiratory mask 10 receives the first gas FA and releases a second gas SA in order to supply a user's motion of respiratory system.

The respiratory mask 10 includes a main part 12, an air chamber exchange part 14, an insert 16 and a clamping part 18.

Figure 2:
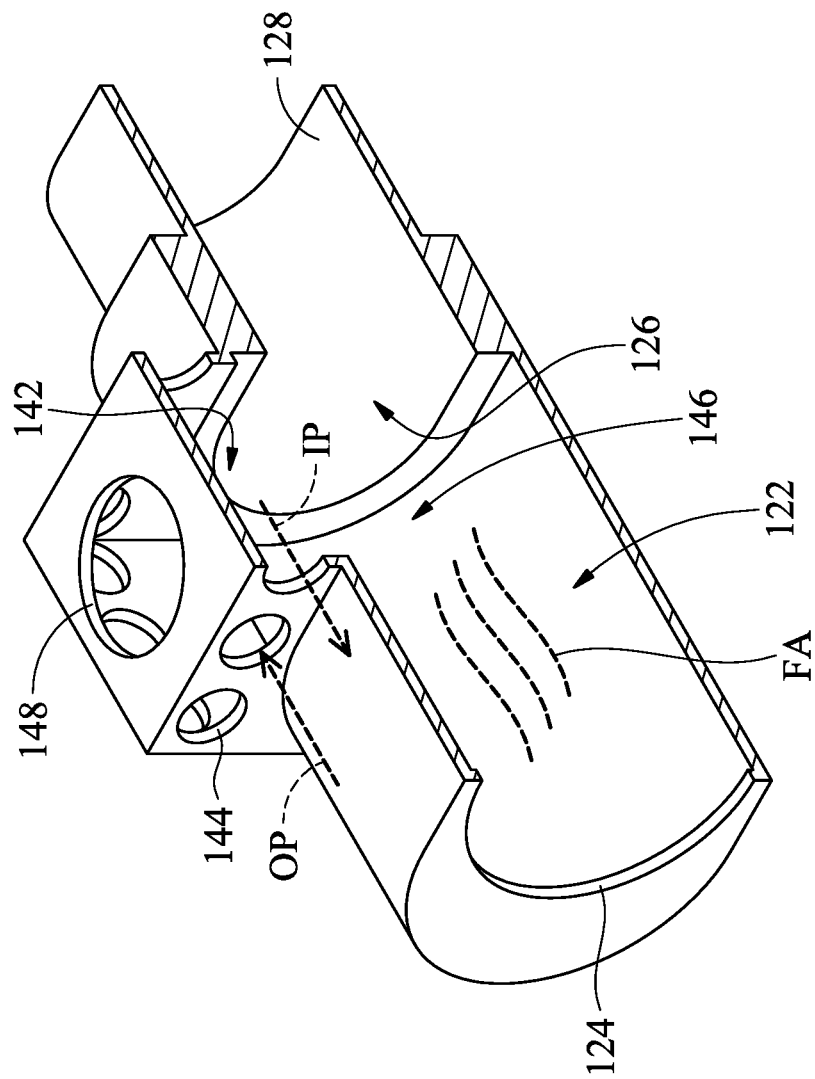
FIG. 2 is a cross-sectional view showing the X-X' of the body and the air chamber exchange part of the first embodiment in the present invention.

The main part 12 includes a first air chamber 122, a first opening 124, a second opening 126 and a third opening 128. Also refer to FIG. 2, a cross-sectional view showing the X-X' of the body and the air chamber exchange part of the first embodiment in the present invention.

In this embodiment, the main part 12 is illustrated by taking a columnar body as an example. The first air chamber 122 is formed in the columnar body, and the first opening 124 and the third opening 128 are respectively formed in two sides the columnar body. The second opening 126 is formed in the upper side of the columnar body.

The first opening 124, the second opening 126 and the third opening 128 are elliptical, circular, square, rectangular, quadrangular and etc. In this embodiment, the first opening 124, the second opening 126 and the third opening 128 are illustrated by a circular shape as an example. The first opening 122 and the second opening 124 are communicated each other by the first air chamber 122. In other embodiments, the first opening 122, the second opening 124 and the third opening 126 may also be communicated each other through the first air chamber 122. The first opening 124 connects to the breathing tube to receive the first gas FA so that the first gas chamber 122 is filled with the first gas FA.

The air chamber exchange part 14 includes a second air chamber 142, an exhaust assembly 144, a fourth opening 146 and a fifth opening 148.

In this embodiment, the main part 12 is illustrated by taking a rectangular body as an example. The second air chamber 142 is formed in the rectangular body, the exhaust assembly 144 is formed at a periphery of the air chamber exchange part 14, and the second opening 126 is jointed with the fourth opening 146. Since the fourth opening 146 is jointed with the second opening 126, the first gas FA moves from the first air chamber 122 to the second air chamber 142, or the second gas SA moves from the second air chamber 142 to the first air chamber 122.

In this embodiment, the exhaust assembly 144 is exemplified by plurality. In other embodiments, the number of exhaust assembly 144 can be single. The exhaust assembly 144 can be configured in many ways. For example, the exhaust assembly 144 may be composed of a gate (not shown) and a cover (not shown). Wherein, the cover can cover and close the gate to block communication between the second air chamber 142 and the outside of the air chamber exchange part 14, so that the second air chamber 142 can release gas; The cover forms an opening at an angle with the gate so that the second air chamber 142 is communicated with the outside of the air chamber exchange part 14. For explanation of the operation principle of the exhaust assembly 144, an internal air pressure IP is provided by the second air chamber 142 and an external air pressure OP (e.g., atmosphere) is provided by the outside of the respiratory mask 10.

For example, when the internal air pressure IP is greater than the external air pressure OP, mainly the internal air pressure IP is applied to the cover, the cover forms an opening with the gate at an angle and causes the exhaust assembly 144 to communicate the second air chamber 142 with the outside of the air chamber exchange part 14 and vice versa. When the internal air pressure IP is smaller than the external air pressure OP, mainly the external air pressure OP is applied to the cover, the cover continues to cover the gate such that the exhaust assembly 144 does not communicate the second air chamber 142 with the outside of the air chamber exchange part 14.

In another embodiment, the action mentioned above may cause the reverse action because of the structure of the exhaust assembly 144. That is, the internal air pressure is smaller than the external air pressure, and the exhaust assembly communicates the outside of the second air chamber with the air chamber exchange part; Alternatively, the internal air pressure is greater than the external air pressure, and the exhaust assembly does not communicate the outside of the second air chamber with the air chamber exchange part.

In general, the exhaust assembly 144 can determine whether to communicate the second air chamber 142 with the outside of the air chamber exchange part 14 or not according to an internal air pressure IP and an external air pressure OP of the second air chamber 142.

Figure 3:
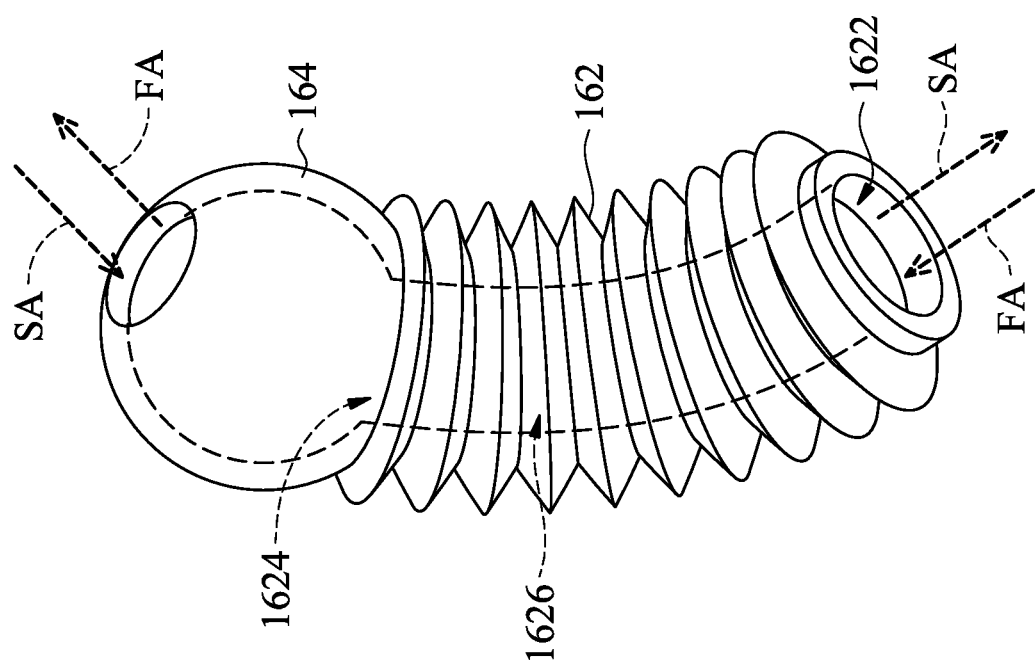
FIG. 3 is a stereograph showing the insert of the first embodiment in the present invention.

The insert 16 connects to the fifth opening 148. The insert 16 connects to the user's nose (not shown). The insert 16 directs the first gas FA to the user or directs the second gas SA from the user to the second air chamber 142. Also refer to FIG. 3, a stereograph of the insert of the first embodiment in the present invention. In FIG. 3, the insert 16 also includes a tubular body 162 having a first end surface 1622 and a second end surface 1624. The first end face 1622 connects the fifth opening 148, the second end face 1622 connects the user's nose, and the tubular body 162 provides a gas channel 1626 for receiving the second gas SA exhaled from the user's nose.

The tubular body 162 is a telescopic structure, such that it can change a length of the tubular body 162 by deformation of the telescopic structure to be adapted to different users. The insert 16 further includes a sealing part 164. The sealing part 164 is disposed on the second end surface 1624 for insertion into the user's nostril.

Figure 4:
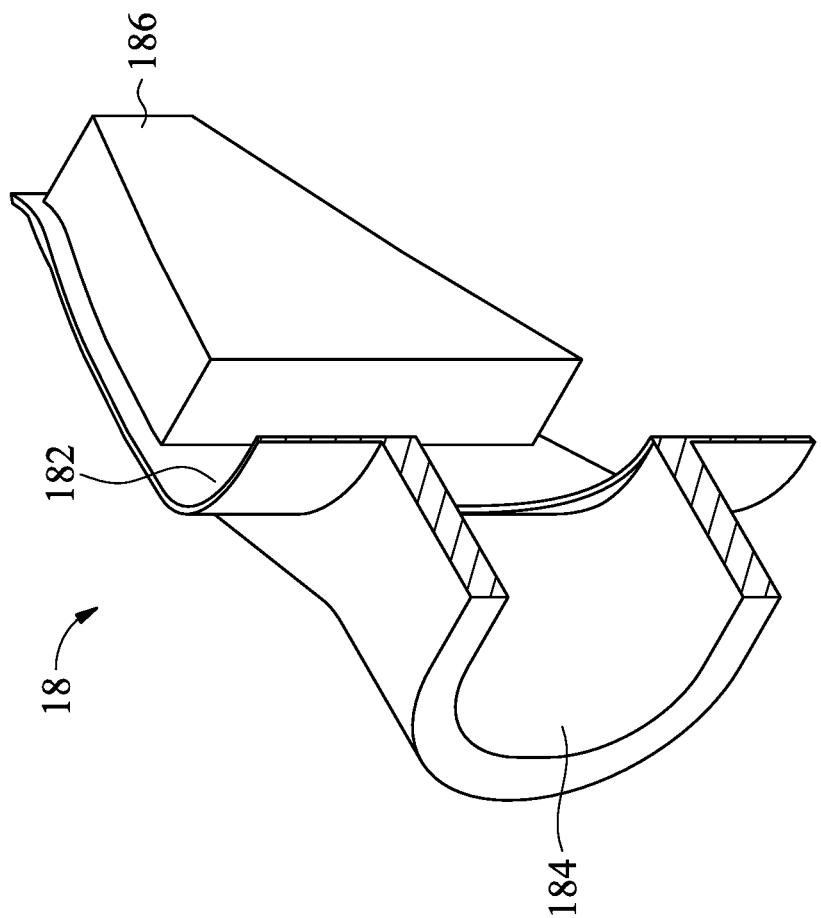
FIG. 4 is a cross-sectional view showing the X-X' of the clamping part of the first embodiment in the present invention.

The clamping part 18 connects to the third opening 128. The clamping part 18 connects to the user's mouth. Refer to FIG. 4, cross-sectional view of the X-X' of the clamping part of the first embodiment in the present invention. In FIG. 4, the clamping part 18 includes a cover part 182, a connecting part 184 and a teeth protection part 186. A cover part 182 is disposed in the periphery of the connecting part 184 for covering the user's mouth. The connecting part 184 connects to the third opening 128. A teeth protection part 186 is formed inside the cover part 182 to be clamped to teeth and inside of cheek of user so that the user can support the respiratory mask 10 in the correct position. In this embodiment, a width of the two sides of the cover part 182 is smaller than a width of the center side to cover the mouth of the user. In other embodiments, a width of the two sides of the cover part 182 may also be equal to or greater than a width of the center side.

Figure 5:
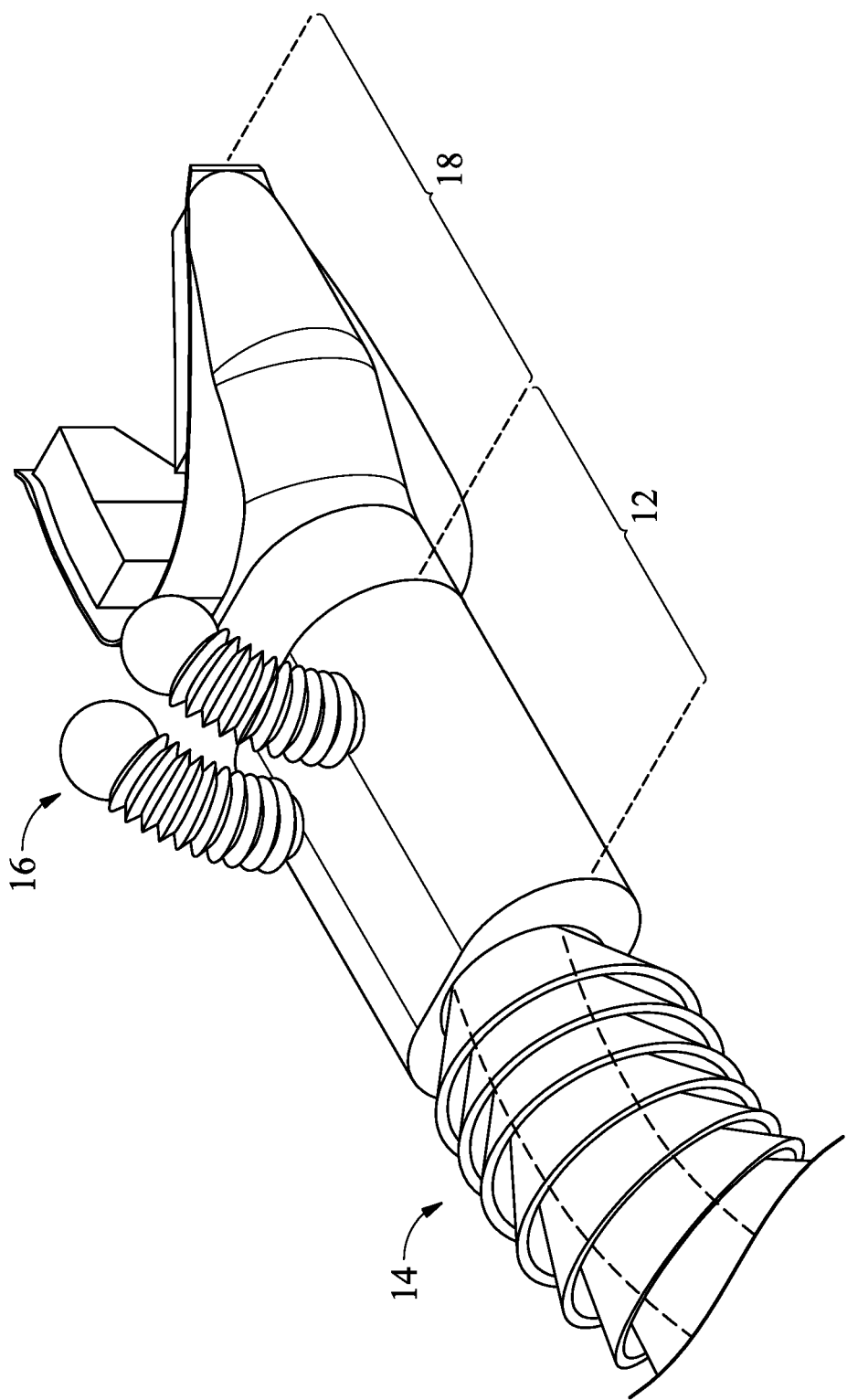
FIG. 5 is a stereograph showing the structure of the respiratory mask of the second embodiment in the present invention.

Please refer to FIG. 5, a stereograph showing the structure of the respiratory mask according to the second embodiment of the present invention. In FIG. 5, the respiratory mask 10' connects to a breathing tube (not shown). In this embodiment, the breathing tube receives a first gas FA from a respirator. The respiratory mask 10' receives the first gas FA and releases second gas SA to supply a user's motion of respiratory system. Except that the respiratory mask 10' includes the main part 12, the insert 16 and the clamping part 18 of the first embodiment, the difference thereof is an air chamber exchange part 14'.

The description of the main part 12, the insert 16 and the clamping part 18 is same as that of the first embodiment. The difference is that in this embodiment the first opening 124 connects to the air chamber exchange part 14' and the insert part 16 to connect to, for example, the first air chamber 122 in the first embodiment.

The air chamber exchange part 14' includes a second air chamber 142', an exhaust assembly 144', a fourth opening 146' and a fifth opening 148'.

The exhaust assembly 144' is formed at the periphery of the air chamber exchange part 14'. In this embodiment, the air chamber exchange part 14' is composed of a plurality of conical cup bodies which are connected in a stack to form the exhaust assembly 144' between the plurality of conical cup bodies, and the second gas SA can be released from the exhaust assembly 144'.

The fourth opening 146' connects to the breathing tube to receive the first gas FA from the breathing tube. The fifth opening 148' is jointed with the first opening 124. The exhaust air assembly 144' determines whether to communicate the second air chamber 142' with the outside of the air chamber exchange part 14' or not according to an internal air pressure and an external air pressure of the second air chamber 142'.

In this embodiment, the insert 16 can guide the second gas SA to the user or guide the second gas SA from the user to the first chamber 122 and second air chamber 142.

The present invention has disclosed with preferred embodiments in the foregoing paragraphs, and it should be understood by those skilled professionals in the operations that the present invention is only intended to depict the invention and should not be limited to the scope of the present invention. It should be noted that variations and permutations equivalent to those of the embodiments are intended to be fallen into the scope of the present invention. Therefore, the scope of protection of the present invention is subject to the definition of the scope of patent application.

What is claimed is:

1. A respiratory mask connected to a breathing tube for receiving a first gas and releasing a second gas to supply a user's motion of respiratory system, the respiratory mask comprises:
   a main part having a first air chamber, a first opening, a second opening and a third opening, the first opening is communicated with the second opening through the first air chamber;
   an air chamber exchange part having a second air chamber, an exhaust assembly, a fourth opening and a fifth opening, the exhaust assembly is formed at a periphery of the air chamber exchange part, the fourth opening is connected to the breathing tube to receive the first gas from the breathing tube, the fifth opening is jointed with the first opening, wherein the exhaust assembly determines whether to communicate the second air chamber and an outside of the air chamber exchange part or not according to an internal air pressure and an external air pressure of the second air chamber;
   an insert connected to the first air chamber, the insert is connected to the user's nose, and the insert guides the second gas to the user or guides the second gas from the user to the first air chamber and the second air chamber;
   a clamping part connected to the third opening, the clamping part is connected to the user's mouth; and
   the air chamber exchange part is composed of a plurality of conical cup bodies, the plurality of conical cup bodies are connected in a stack so that the exhaust assembly is formed between the plurality of conical cup bodies.

2. The respiratory mask according to claim 1, wherein a shape of the first opening, the second opening and the third opening is at least one of an elliptical shape, a circular shape, a square shape, a rectangular shape and a quadrangular shape.

3. The respiratory mask according to claim 1, wherein when the internal air pressure is greater than the external air pressure, the second air chamber is communicated with the outside of the air chamber exchange part by the exhaust assembly, and when the internal air pressure is less than the external air pressure, the second air chamber is not communicated with the outside of the air chamber exchange part by the exhaust assembly.

4. The respiratory mask according to claim 1, wherein when the internal air pressure is less than the external air pressure, the second air chamber is communicated with the outside of the air chamber exchange part by the exhaust assembly, and when the internal air pressure is greater than the external air pressure, the second air chamber is not communicated with the outside of the air chamber exchange part by the exhaust assembly.

5. The respiratory mask according to claim 3, wherein a number of the exhaust assembly is one or plural.

6. The respiratory mask according to claim 4, wherein a number of the exhaust assembly is one or plural.

7. The respiratory mask according to claim 1, wherein the insert further comprises a tubular body of a first end surface and a second end surface, the first end surface is connected to the second opening and the second end surface is connected to the user's nose and the tubular body provides a gas tunnel.

8. The respiratory mask according to claim 7, wherein the tubular body has a telescopic structure to change a length of the tubular body by deformation of the telescopic structure.

9. The respiratory mask according to claim 7, wherein the insert further comprises a sealing part, the sealing part is disposed on the second end surface for insertion into the user's nostril.

10. The respiratory mask according to claim 1, wherein the clamping part further comprises a cover part, a connecting part and a teeth protection part, the cover part is disposed in a periphery of the connecting part to cover the user's mouth, the connecting part is connected to the third opening, and the teeth protection part is formed inside of the cover part to be clamped to teeth and inside of cheek of the user.

11. The respiratory mask according to claim 10, wherein a width of the two sides of the cover part is not greater than a width of the center side.

* * * * *